(12) United States Patent
Hunter et al.

(10) Patent No.: US 6,235,038 B1
(45) Date of Patent: May 22, 2001

(54) SYSTEM FOR TRANSLATION OF ELECTROMAGNETIC AND OPTICAL LOCALIZATION SYSTEMS

(75) Inventors: Mark W. Hunter; Paul Kessman, both of Broomfield, CO (US)

(73) Assignee: Medtronic Surgical Navigation Technologies, Louisville, CO (US)

( * ) Notice: Subject to any disclaimer, the term of this patent is extended or adjusted under 35 U.S.C. 154(b) by 0 days.

(21) Appl. No.: 09/429,568

(22) Filed: Oct. 28, 1999

(51) Int. Cl.$^7$ ................................................ A61B 19/00
(52) U.S. Cl. ......................... 606/130; 600/429; 600/417
(58) Field of Search ................................. 606/130, 129, 606/1, 79, 80, 96, 60, 61, 62, 104; 600/426, 414, 417, 429, 424, 407

(56) References Cited

U.S. PATENT DOCUMENTS

| | | | |
|---|---|---|---|
| Re. 35,816 | 6/1998 | Schulz | 356/376 |
| 2,650,588 | 9/1953 | Drew | 128/92 |
| 3,868,565 | 2/1975 | Kuipers | 324/34 R |
| 3,983,474 | 9/1976 | Kuipers | 324/43 R |
| 4,173,228 | 11/1979 | Van Steenwyk et al. | 128/653 |
| 4,182,312 | 1/1980 | Mushabac | 433/68 |
| 4,202,349 | 5/1980 | Jones | 128/689 |
| 4,314,251 | 2/1982 | Raab | 343/112 R |
| 4,317,078 | 2/1982 | Weed et al. | 324/208 |
| 4,339,953 | 7/1982 | Iwasaki | 73/654 |
| 4,396,945 | 8/1983 | DiMatteo et al. | 358/107 |
| 4,419,012 | 12/1983 | Stephenson et al. | 356/141 |
| 4,422,041 | 12/1983 | Lienau | 324/207 |
| 4,431,005 | 2/1984 | McCormick | 128/656 |
| 4,571,834 | 2/1986 | Fraser et al. | 33/1 PT |
| 4,583,538 | 4/1986 | Onik et al. | 128/303 B |
| 4,613,866 | 9/1986 | Blood | 343/448 |
| 4,618,978 | 10/1986 | Cosman | 378/164 |
| 4,642,786 | 2/1987 | Hansen | 364/559 |
| 4,651,732 | 3/1987 | Frederick | 128/303 R |
| 4,673,352 | 6/1987 | Hansen | 433/69 |
| 4,722,056 | 1/1988 | Roberts et al. | 364/413 |

(List continued on next page.)

FOREIGN PATENT DOCUMENTS

| | | | |
|---|---|---|---|
| 3717871 A1 | 12/1988 | (DE) | A61B/19/00 |
| 3717871 C2 | 12/1988 | (DE) | A61B/19/00 |
| 3838011 A1 | 7/1989 | (DE) | A61B/19/00 |

(List continued on next page.)

OTHER PUBLICATIONS

Adams, L., et al., *Computer–Assisted Surgery*, IEEE Computer Graphics & Applications, pp. 43–51 (May 1990).

Adams, L., et al., *Aide au Reperage Tridimensionnel pour la Chirurgie de la Base du Crane*, Innov. Tech. Biol. Med., vol. 13, No. 4, pp. 409–424 (1992).

Benzel, E., et al., *Magnetic Source Imaging: A Review of the Magnes System of Biomagnetic Technologies Incorporated*, Neurosurgery, vol. 33, No. 2, (Aug. 1993).

(List continued on next page.)

*Primary Examiner*—Pedro Philogene
(74) *Attorney, Agent, or Firm*—Finnegan, Henderson, Farabow, Garrett & Dunner LLP

(57) ABSTRACT

A system for utilizing and registering at least two surgical navigation systems during stereotactic surgery. The system comprises a first surgical navigation system defining a first patient space, a second surgical navigation system defining a second patient space, and a translation device to register the coordinates of the first patient space to the coordinates of the second patient space. The translation device comprises a rigid body, at least one component for a first navigation system placed in or on the rigid body, and at least one component for a second navigation system placed in or on the rigid body, in known relation to the at least one component for the first navigation system. The translation device is positioned in a working volume of each of the at least two navigation systems.

19 Claims, 2 Drawing Sheets

U.S. PATENT DOCUMENTS

| | | | |
|---|---|---|---|
| 4,737,794 | 4/1988 | Jones | 342/448 |
| 4,791,934 | 12/1988 | Brunnett | 128/653 |
| 4,793,355 | 12/1988 | Crum et al. | 128/653 |
| 4,821,731 | 4/1989 | Martinelli et al. | 128/662.06 |
| 4,836,778 | 6/1989 | Baumrind et al. | 433/69 |
| 4,849,692 | 7/1989 | Blood | 324/208 |
| 4,896,673 | 1/1990 | Rose et al. | 128/660.03 |
| 4,905,698 | 3/1990 | Strohl, Jr. et al. | 128/653 R |
| 4,945,305 | 7/1990 | Blood | 324/207.17 |
| 4,945,914 | 8/1990 | Allen | 128/653 R |
| 4,991,579 | 2/1991 | Allen | 128/653 R |
| 5,016,639 | 5/1991 | Allen | 128/653 R |
| 5,042,486 | 8/1991 | Pfeiler et al. | 128/653 R |
| 5,047,036 | 9/1991 | Koutrouvelis et al. | 606/130 |
| 5,059,789 | 10/1991 | Salcudean | 250/206.1 |
| 5,078,140 | 1/1992 | Kwoh | 128/653.1 |
| 5,086,401 | 2/1992 | Glassman et al. | 395/94 |
| 5,094,241 | 3/1992 | Allen | 128/653.1 |
| 5,097,839 | 3/1992 | Allen | 128/653.1 |
| 5,099,845 | 3/1992 | Besz et al. | 128/653.1 |
| 5,107,839 | 4/1992 | Houdek et al. | 128/653.1 |
| 5,119,817 | 6/1992 | Allen | 128/653.1 |
| 5,142,930 | 9/1992 | Allen et al. | 74/469 |
| 5,152,288 | 10/1992 | Hoening et al. | 128/653.1 |
| 5,160,337 | 11/1992 | Cosman | 606/130 |
| 5,178,164 | 1/1993 | Allen | 128/898 |
| 5,186,174 | 2/1993 | Schlondorff et al. | 128/653.1 |
| 5,187,475 | 2/1993 | Wagener et al. | 340/870.32 |
| 5,193,106 | 3/1993 | DeSena | 378/673 |
| 5,197,476 | 3/1993 | Nowacki et al. | 128/660.03 |
| 5,198,877 | 3/1993 | Schulz | 356/375 |
| 5,211,164 | 5/1993 | Allen | 128/653.1 |
| 5,211,165 | 5/1993 | Dumoulin et al. | 128/653.1 |
| 5,214,615 | 5/1993 | Bauer | 367/128 |
| 5,222,499 | 6/1993 | Allen et al. | 128/653.1 |
| 5,230,338 | 7/1993 | Allen et al. | 128/653 |
| 5,230,623 | 7/1993 | Guthrie et al. | 433/72 |
| 5,249,581 | 10/1993 | Horbal et al. | 128/664 |
| 5,251,127 | 10/1993 | Raab | 364/413.13 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,261,404 | 11/1993 | Mick et al. | 128/653.1 |
| 5,265,610 | 11/1993 | Darrow et al. | 128/653.1 |
| 5,265,611 | 11/1993 | Hoenig et al. | 128/653.1 |
| 5,274,551 | 12/1993 | Corby, Jr. | 364/413.13 |
| 5,279,309 | 1/1994 | Taylor et al. | 128/782 |
| 5,291,889 | 3/1994 | Kenet et al. | 128/653.1 |
| 5,295,483 | 3/1994 | Nowacki et al. | 128/660 |
| 5,299,254 | 3/1994 | Dancer et al. | 378/163 |
| 5,299,288 | 3/1994 | Glassman et al. | 395/80 |
| 5,305,203 | 4/1994 | Raab | 364/413.13 |
| 5,309,913 | 5/1994 | Kormos et al. | 128/653.1 |
| 5,315,630 | 5/1994 | Sturm et al. | 378/65 |
| 5,316,024 | 5/1994 | Hischi et al. | 128/899 |
| 5,318,025 | 6/1994 | Dumoulin et al. | 128/653.2 |
| 5,325,873 | 7/1994 | Hirschi et al. | 128/899 |
| 5,353,795 | 10/1994 | Souza et al. | 128/653.2 |
| 5,353,807 | 10/1994 | DeMarco | 128/772 |
| 5,359,417 | 10/1994 | Muller et al. | 356/375 |
| 5,368,030 | 11/1994 | Zinreich et al. | 128/653.1 |
| 5,371,778 | 12/1994 | Yanof et al. | 364/413.22 |
| 5,377,678 | 1/1995 | Dumoulin et al. | 128/653.1 |
| 5,383,454 | 1/1995 | Bucholz | 128/653.1 |
| 5,389,101 | 2/1995 | Heilbrun et al. | 606/130 |
| 5,391,199 | 2/1995 | Ben-Haim | 607/122 |
| 5,397,329 | 3/1995 | Allen | 606/73 |
| 5,398,684 | 3/1995 | Hardy | 128/653.1 |
| 5,402,801 | 4/1995 | Taylor | 128/898 |
| 5,408,409 | 4/1995 | Glassman et al. | 364/413.13 |
| 5,413,573 | 5/1995 | Koivukangas | 606/1 |
| 5,419,325 | 5/1995 | Dumoulin et al. | 128/653.2 |
| 5,425,367 | 6/1995 | Shapiro et al. | 128/653.1 |
| 5,425,382 | 6/1995 | Golden et al. | 128/899 |
| 5,429,132 | 7/1995 | Guy et al. | 128/653.1 |
| 5,437,277 | 8/1995 | Dumoulin et al. | 128/653.1 |
| 5,443,066 | 8/1995 | Dumoulin et al. | 128/653.1 |
| 5,443,489 | 8/1995 | Ben-Haim | 607/115 |
| 5,445,150 | 8/1995 | Dumoulin et al. | 128/653.1 |
| 5,446,548 | 8/1995 | Gerig et al. | 356/375 |
| 5,447,154 | 9/1995 | Cinquin et al. | 128/653.1 |
| 5,453,686 | 9/1995 | Anderson | 324/207.17 |
| 5,456,718 | 10/1995 | Szymaitis | 623/11 |
| 5,480,422 | 1/1996 | Ben-Haim | 607/122 |
| 5,483,961 * | 1/1996 | Kelly et al. | 606/130 |
| 5,494,034 | 2/1996 | Schlöndorff et al. | 128/653.1 |
| 5,515,160 | 5/1996 | Schulz et al. | 356/241 |
| 5,517,990 | 5/1996 | Kalfas et al. | 128/653.1 |
| 5,531,227 | 7/1996 | Schneider | 128/653.1 |
| 5,531,520 | 7/1996 | Grimson et al. | 382/131 |
| 5,546,951 | 8/1996 | Ben-Haim | 128/702 |
| 5,551,429 | 9/1996 | Fitzpatrick et al. | 128/653.1 |
| 5,558,091 | 9/1996 | Acker et al. | 128/653.1 |
| 5,568,809 | 10/1996 | Ben-Haim | 128/656 |
| 5,572,999 | 11/1996 | Funda et al. | 128/653.1 |
| 5,575,798 | 11/1996 | Koutrouvelis | 606/130 |
| 5,588,430 | 12/1996 | Bova et al. | 128/653.1 |
| 5,590,215 | 12/1996 | Allen | 382/128 |
| 5,592,939 | 1/1997 | Martinelli | 128/653.1 |
| 5,600,330 | 2/1997 | Blood | 342/463 |
| 5,603,318 | 2/1997 | Heilbrun et al. | 128/630 |
| 5,611,025 | 3/1997 | Lorensen et al. | 395/119 |
| 5,617,857 | 4/1997 | Chader et al. | 128/653.1 |
| 5,622,169 | 4/1997 | Golden et al. | 128/653.1 |
| 5,622,170 | 4/1997 | Schulz | 128/653.1 |
| 5,630,431 | 5/1997 | Taylor | 128/897 |
| 5,638,819 | 6/1997 | Manwaring et al. | 128/653.1 |
| 5,640,170 | 6/1997 | Anderson | 343/895 |
| 5,645,065 | 7/1997 | Shapiro et al. | 128/653.1 |
| 5,647,361 | 7/1997 | Damadian | 128/683.2 |
| 5,662,111 | 9/1997 | Cosman | 128/653.1 |
| 5,676,673 | 10/1997 | Ferre et al. | 606/130 |
| 5,681,260 | 10/1997 | Ueda et al. | 600/114 |
| 5,682,886 | 11/1997 | Delp et al. | 128/653.1 |
| 5,682,890 | 11/1997 | Kormos et al. | 128/653.2 |
| 5,694,945 | 12/1997 | Ben-Haim | 128/736 |
| 5,695,500 | 12/1997 | Taylor et al. | 606/130 |
| 5,695,501 | 12/1997 | Carol et al. | 606/130 |
| 5,697,377 | 12/1997 | Wittkampf | 128/696 |
| 5,711,299 | 1/1998 | Manwaring et al. | 128/653.1 |
| 5,713,946 | 2/1998 | Ben-Haim | 607/122 |
| 5,715,822 | 2/1998 | Watkins et al. | 128/653.5 |
| 5,718,241 | 2/1998 | Ben-Haim et al. | 128/702 |
| 5,727,552 | 3/1998 | Ryan | 128/653.1 |
| 5,727,553 | 3/1998 | Saad | 128/653.1 |
| 5,729,129 | 3/1998 | Acker | 324/207.12 |
| 5,730,129 | 3/1998 | Darrow et al. | 128/653.1 |
| 5,730,130 | 3/1998 | Fitzpatrick et al. | 128/653.1 |
| 5,732,703 | 3/1998 | Kalfas et al. | 128/653.1 |
| 5,738,096 | 4/1998 | Ben-Haim | 128/653.1 |
| 5,740,802 | 4/1998 | Nafis et al. | 128/653.1 |
| 5,742,394 | 4/1998 | Hansen | 356/375 |
| 5,744,953 | 4/1998 | Hansen | 324/207.17 |
| 5,748,767 | 5/1998 | Raab | 382/128 |
| 5,749,362 | 5/1998 | Funda et al. | 128/653.1 |
| 5,752,513 | 5/1998 | Acker et al. | 128/653.1 |
| 5,755,725 | 5/1998 | Druais | 606/130 |
| 5,762,064 | 6/1998 | Polvani | 128/653.1 |
| 5,767,669 | 6/1998 | Hansen et al. | 324/207.12 |
| 5,767,960 | 6/1998 | Orman | 356/139.03 |
| 5,769,789 | 6/1998 | Wang et al. | 600/414 |

| | | | |
|---|---|---|---|
| 5,769,843 | 6/1998 | Abela et al. ............................ 606/10 |
| 5,769,861 | 6/1998 | Vilsmeier ............................. 606/130 |
| 5,772,594 | 6/1998 | Barrick ................................. 600/407 |
| 5,776,064 | 7/1998 | Kalfas et al. ........................ 600/414 |
| 5,782,765 | 7/1998 | Jonkman ............................... 600/424 |
| 5,787,886 * | 8/1998 | Kelley et al. ........................ 606/130 |
| 5,795,294 | 8/1998 | Luber et al. ........................ 600/407 |
| 5,797,849 | 8/1998 | Vesely et al. ........................ 600/461 |
| 5,799,055 | 8/1998 | Peshkin et al. ....................... 378/42 |
| 5,800,352 | 9/1998 | Ferre et al. .......................... 600/407 |
| 5,820,553 | 10/1998 | Hughes ................................ 600/426 |
| 5,823,958 | 10/1998 | Truppe ................................. 600/426 |
| 5,828,770 | 10/1998 | Leis et al. ............................ 382/103 |
| 5,829,444 | 11/1998 | Ferre et al. .......................... 128/897 |
| 5,831,260 | 11/1998 | Hansen ................................ 250/221 |
| 5,833,608 | 11/1998 | Acker .................................. 600/409 |
| 5,834,759 | 11/1998 | Glossop ............................. 250/203.1 |
| 5,836,954 | 11/1998 | Heilbrun et al. ..................... 606/130 |
| 5,840,025 | 11/1998 | Ben-Haim ............................ 600/424 |
| 5,848,967 | 12/1998 | Cosman ................................ 600/426 |
| 5,851,183 | 12/1998 | Bucholz ............................... 600/425 |
| 5,868,675 | 2/1999 | Henrion et al. ...................... 600/424 |
| 5,871,445 | 2/1999 | Bucholz ............................... 600/407 |
| 5,873,822 | 2/1999 | Ferre et al. .......................... 600/407 |
| 5,882,304 | 3/1999 | Ehnholm et al. .................... 600/411 |
| 5,884,410 | 3/1999 | Prinz .................................... 33/559 |
| 5,891,034 | 4/1999 | Bucholz ............................... 600/426 |
| 5,904,691 | 5/1999 | Barnett et al. ........................ 606/130 |
| 5,907,395 | 5/1999 | Schulz et al. ..................... 356/139.03 |
| 5,913,820 | 6/1999 | Bladen et al. ....................... 600/407 |
| 5,920,395 | 7/1999 | Schulz ................................. 356/375 |
| 5,921,992 | 7/1999 | Costales et al. ...................... 606/130 |
| 5,938,603 | 8/1999 | Ponzi .................................... 600/424 |
| 5,947,981 | 9/1999 | Cosman ............................... 606/130 |
| 5,954,647 | 9/1999 | Bova et al. .......................... 600/407 |
| 5,967,982 | 10/1999 | Barnett ................................. 600/429 |
| 5,971,997 | 10/1999 | Guthrie et al. ....................... 606/130 |
| 5,980,535 | 11/1999 | Barnett et al. ........................ 606/130 |
| 5,987,349 | 11/1999 | Schultz ................................. 600/427 |
| 5,987,960 | 11/1999 | Messner et al. ...................... 73/1.79 |
| 5,999,837 | 12/1999 | Messner et al. ...................... 600/407 |
| 5,999,840 | 12/1999 | Grimson et al. ..................... 600/424 |
| 6,006,126 | 12/1999 | Cosman ............................... 600/426 |
| 6,006,127 | 12/1999 | Van Der Brug et al. ............ 600/427 |
| 6,013,087 | 1/2000 | Adams et al. ........................ 606/130 |
| 6,014,580 | 1/2000 | Blume et al. ........................ 600/424 |
| 6,015,414 * | 1/2000 | Werp et al. ........................... 606/130 |
| 6,016,439 | 1/2000 | Acker ................................... 600/411 |
| 6,019,725 | 2/2000 | Vesely et al. ........................ 600/447 |
| 6,021,343 * | 2/2000 | Foley et al. ........................... 600/417 |
| 6,026,315 * | 2/2000 | Lenz et al. ............................ 600/414 |
| 6,080,164 * | 6/2000 | Oshio et al. .......................... 606/130 |
| B1 5,383,454 | 12/1996 | Bucholz ............................. 128/653.1 |

FOREIGN PATENT DOCUMENTS

| | | | |
|---|---|---|---|
| 4225112 C1 | 12/1993 | (DE) ............................... A61B/19/00 |
| 4233978 | 4/1994 | (DE) ............................... A61B/19/00 |
| 19715202 A1 | 10/1998 | (DE) ............................... A61B/19/00 |
| 19751761 A1 | 10/1998 | (DE) ............................... A61B/19/00 |
| 19832296 A1 | 2/1999 | (DE) ................................. G01J/1/42 |
| 19747427 A1 | 5/1999 | (DE) ............................... A61B/19/00 |
| 0 155 857 A2 | 9/1985 | (EP) ................................. G01B/7/00 |
| 0 326 768 A2 | 8/1989 | (EP) ............................... A61B/19/00 |
| 0 359 773 B1 | 3/1990 | (EP) ................................. A61B/6/02 |
| 0 419 729 A1 | 4/1991 | (EP) ................................. A61B/5/06 |
| 0 427 358 A1 | 5/1991 | (EP) ................................. A61B/6/00 |
| 0 456 103 A2 | 11/1991 | (EP) ............................... A61B/19/00 |
| 0 469 966 A1 | 2/1992 | (EP) ............................... A61B/19/00 |
| 0 501 993 B1 | 9/1992 | (EP) ............................... G06T/17/00 |
| 0 581 704 A1 | 2/1994 | (EP) ................................. A61B/8/14 |
| 0 655 138 B1 | 5/1995 | (EP) ................................. G01S/3/14 |
| 0 894 473 A2 | 2/1999 | (EP) ................................. A61B/8/12 |
| 0 908 146 A2 | 4/1999 | (EP) ............................... A61B/17/17 |
| 0 930 046 A2 | 7/1999 | (EP) ................................. A61B/6/00 |
| WO 88/09151 | 12/1988 | (WO) ............................. A61B/19/00 |
| WO 90/05494 | 5/1990 | (WO) ............................. A61B/19/00 |
| WO 91/04711 | 4/1991 | (WO) ............................. A61B/19/00 |
| WO 91/07726 | 5/1991 | (WO) ............................. G06F/15/72 |
| WO 92/06645 | 4/1992 | (WO) ............................. A61B/19/00 |
| WO 94/04938 | 3/1994 | (WO) ............................... G01S/3/14 |
| WO 94/23647 | 10/1994 | (WO) ............................... A61B/5/05 |
| WO 94/24933 | 11/1994 | (WO) ............................... A61B/5/05 |
| WO 95/07055 | 3/1995 | (WO) ............................. A61B/19/00 |
| WO 96/11624 | 4/1996 | (WO) . |
| WO 96/32059 | 10/1996 | (WO) ............................. A61B/5/055 |
| WO 97/36192 | 10/1997 | (WO) ............................. G01V/15/00 |
| WO 97/49453 | 12/1997 | (WO) ............................... A61N/1/36 |
| WO 98/38908 | 9/1998 | (WO) ............................... A61B/5/00 |
| WO 99/15097 | 4/1999 | (WO) ............................. A61B/19/00 |
| WO 99/21498 | 5/1999 | (WO) ............................. A61B/17/56 |
| WO 99/23956 | 5/1999 | (WO) ............................. A61B/17/17 |
| WO 99/26549 | 6/1999 | (WO) ............................. A61B/19/00 |
| WO 99/27839 | 6/1999 | (WO) . |
| WO 99/29253 | 6/1999 | (WO) ............................. A61B/19/00 |
| WO 99/33406 | 7/1999 | (WO) ............................. A61B/19/00 |
| WO 99/38449 | 8/1999 | (WO) ............................. A61B/19/00 |
| WO 99/52094 | 10/1999 | (WO) ............................... G09G/3/02 |

OTHER PUBLICATIONS

Bergstrom, M., et al., *Stereotaxic Computed Tomography*, Am. J. Roentgenol, vol. 127 pp. 167–170 (1976).

Bucholz, R.D., et al., *Variables affecting the accuracy of stereotactic localization using computerized tomography*, J. Neurosurg., vol. 79, pp. 667–673 (1993).

Bucholz, R.D., et al., *A Comparison of Sonic Digitizers Versus Light Emitting Diode–Based Localization*, Interactive Image–guided Neurosurgery, Chapter 16, pp. 179–200 (1993).

Bucholz, R.D., et al., *Intraoperative localization using a three dimensional optical digitizer*, SPIE—The Intl. Soc. for Opt. Eng., vol. 1894, pp. 312–322 (Jan. 17–19, 1993).

Bucholz, R.D., et al., *Image–guided surgical techniques for infections and trauma of the central nervous system*, Neurosurg. Clinics of N.A., vol. 7, No. 2, pp. 187–200 (1996).

Bucholz, R.D., et al., *The Correction of Stereotactic Inaccuracy Caused by Brain Shift Using an Intraoperative Ultrasound Device*, First Joint Conference, Computer Vision, Virtual Reality and Robotics in Medicine and Medical Robotics and Computer–Assisted Surgery, Grenoble, France, pp. 459–466 (Mar. 19–22, 1997).

Cinquin, P., et al., *Computer Assisted Medical Interventions*, IEEE, pp. 254–263 (May/Jun. 1995).

Clarysse, P., et al., *A Computer–Assisted System for 3–D Frameless Localization in Stereotaxic MRI*, IEEE Trans. on Med. Imaging, vol. 10, No. 4, pp. 523–529 (Dec. 1991).

Foley, K.T., et al., *Image–guided Intraoperative Spinal Localization*, Intraoperative Neuroprotection, Chapter 19, pp. 325–340 (1996).

Foley, K.T., et al., *The StealthStation™: Three–Dimensional Image–Interactive Guidance for the Spine Surgeon*, Spinal Frontiers, pp. 7–9 (Apr. 1996).

Friets, E.M., et al., *A Frameless Stereotaxic Operating Microscope for Neurosurgery*, IEEE Trans. on Biomed. Eng., vol. 36, No. 6, pp. 608–617 (1989).

Gallen, C.C., et al., *Intracranial Neurosurgery Guided by Functional Imaging*, Surg. Neurol., vol. 42, pp. 523–530 (1994).

Galloway, R.L., et al., *Interactive Image–Guided Neurosurgery*, IEEE Trans. on Biomed. Eng., vol. 89, No. 12, pp 1226–1231 (1992).

Germano, Isabelle M., et al., *The NeuroStation System for Image–Guided, Frameless stereotaxy*, Neurosurg., vol. 37, No. 2, pp. 348–350 (Aug. 1995).

Gomez, C.R., et al., *Transcranial Doppler Ultrasound Following Closed Head Injury: Vasospasm or Vasoparalysis?*, Surg. Neurol., vol. 35, pp. 30–35 (1991).

Grimson, W.E.L., et al., *Virtual–reality technology is giving surgeons the equivalent of x–ray vision helping them to remove tumors. . .* , Sci. Amer., vol. 280, No. 6, pp. 62–69 (Jun. 1999).

Hamadeh, A., et al., *Toward automatic registration between CT and X–ray images: cooperation between 3D/2D registration and 2D edge detection*, TIMC–IMAG, Faculté de Medecine de Grenoble, France, pp. 39–46 (1995)(Second Annual Intl. Symposium on Medical Robotics and Computer–Assisted Surgery, MRCAS '95, Nov. 4–7, 1995).

Hatch, J.F., *Reference–Display System for the Integration of CT Scanning and the Operating Microscope*, IEEE, vol. 8, pp. 252–254, Proceedings of the Eleventh Annual Northeast Bioengineering Conference (Worcester, Massachusetts) (Mar. 14–15, 1985).

Heilbrun, M.P., *Computed Tomography–Guided Stereotactic Systems*, Clinical Neurosurgery, Chapter 31, pp. 564–581 (1983).

Heilbrun, M.P., et al., *Preliminary Experience with Brown–Roberts–Wells (BRW) computerized tomography stereotaxic guidance system*, J. Neurosurg., vol. 59, pp. 217–222 (1983).

Heilbrun, M.P., et al., *Stereotactic localization and Guidance Using a Machine Vision Technique*, Stereotact. Funct. Neurosurg., Proceed. of the Mtg. of the Amer. Soc. for Stereot. and Funct. Neurosurg. (Pittsburgh, PA) vol. 58, pp. 94–98 (1992).

Heilbrun, M.P., *Progressive Technology Applications*, Neurosurgery for the Third Millenium, Chapter 15, pp. 191–198 (1992) (J. Whitaker & Sons Ltd., Amer. Assoc. of Neurol. Surgeons, Oct. 1992).

Henderson, J.M., et al., *An Accurate and Ergonomic Method of Registration for Image–guided Neurosurgery*, Computerized Medical Imaging and Graphics, vol. 18, No. 4, pp. 273–277 (1994).

Hofstetter, R., et al., *Fluoroscopy Based Surgical Navigation–Concept and Clinical Applications*, Computer Assisted Radiology and Surgery, CAR '97, Proceed. of the 11$^{th}$ Intl. Symp. and Exh., Berlin, pp. 956–960 (Jun. 25–28, 1997).

Horner, N.B., et al., *A Comparison of CT–Stereotaxic Brain Biopsy Techniques*, Investig. Radiol., vol. 19, pp. 367–373 (Sep.–Oct. 1984).

Kato, A., et al., *A frameless, armless navigational system for computer–assisted neurosurgery*, J. Neurosurg., vol. 74, pp. 845–849 (May 1991).

Kosugi, Y., et al., *An Articulated Neurosurgical Navigation System Using MRI and CT Images*, IEEE Trans. on Biomed. Eng., vol. 35, No. 2, pp. 147–152 (Feb. 1988).

Krybus, W., et al., *Navigation Support for Surgery by Means of Optical Position Detection*, Computer Assisted Radiology Proceed. of the Intl. Symp. CAR '91 Computed Assisted Radiology, pp. 362–366 (Jul. 3–6, 1991).

Lavallée, S., et al., *A new system for computer assisted neurosurgery*, IEEE EMBS, 11$^{th}$ Annual Intl. Conf., pp. 926–927 (1989).

Lavallée, S., et al., *Computer Assisted Interventionist Imaging: The Instance of Stereotactic Brain Surgery*, MEDINFO 89, pp. 613–617 (1989).

Lavallée, S., et al., *Computer Assisted Medical Interventions*, NATO ASI Series, vol. F 60, 3D Imaging in Medic., pp. 301–312 (1990).

Lavallée, S., et al., *Image guided operating robot: a clinical application in stereotactic neurosurgery*, IEEE Rob. and Autom. Society, Proc. of the 1992 Intl. Conf. on Rob. and Autom., May 1992, pp. 618–624, First Intl. Symp. on Med. Rob. and Comp. Assisted Surg. (Pittsburgh, PA) (Sep. 22–24, 1994).

Lavallée, S., et al., *Computer Assisted Spine Surgery: a technique for accurate transpedicular screw fixation*, TIMC, Faculté de Medecine de Grenoble, J. of Image Guided Surg., vol. 1, No. 1, pp. 65–73 (1995).

Leavitt, D.D., et al., *Dynamic Field Shaping to Optimize Stereotactic Radiosurgery*, I.J. Rad. Onc. Biol. Phys., vol. 21, pp. 1247–1255 (1991).

Lemieux, L., et al., *A patient–to–computed–tomography image registration method based on digitally reconstructed radiographs*, Med. Phys., vol. 21, No. 11, pp. 1749–1760 (1994).

Mazier, B., et al., *Computer assisted interventionist imaging: application to the vertebral column surgery*, Annual Intl. Conf. of the IEEE in Medic. and Biol. Soc., vol. 12, No. 1, pp. 430–431 (1990).

Merloz, P., et al., *Computer assisted Spine Surgery*, Clinical Orthop. and Related Research, No. 337, pp. 86–96 (1997).

Pelizzari, C.A., et al., *Accurate Three–Dimensional Registration of CT, PET, and/or MR Images of the Brain*, Journal of Computer Assisted Tomography, vol. 13, No. 1, pp. 20–26 (Jan./Feb. 1989).

Penn, R.D., et al., *Stereotactic Surgery with Image Processing of Computerized Tomographic Scans*, Neurosurgery, vol. 3, No. 2, pp. 157–153 (Sep.–Oct. 1978).

Reinhardt, H.F., et al., *Mikrochirurgische Entfernung . . . (Microsurgical removal of Deep–Seated Vascular Malformations Using Sonar Stereometry)*, Ultraschall in Med. 12, pp. 80–83 (1991).

Reinhardt, H.F., et al., *Sonic Stereometry in Microsurgical Procedures for Deep–Seated Brain Tumors and Vascular Malformations*, Neurosurgery, vol. 32, No. 1, pp. 51–57 (Jan. 1993).

Roberts, D.W., et al., *A frameless stereotaxic integration of computerized tomographic imaging and the operating microscope*, J. Neurosurg., vol. 65, pp. 545–549 (Oct. 1986).

Simon, D.A., et al., *Accuracy Validation in Image–Guided Orthopaedic Surgery*, Second Annual Intl. Symp. on Med. Rob. and Comp.–Assisted Surgery, MRCAS '95, pp. 185–192 (1995).

Smith, K.R., et al., *Multimodality Image Analysis and Display Methods for Improved Tumor Localization in Stereotactic Neurosurgery*, Annual Intl. Conf. of the IEEE Eng. in Med. and Biol. Soc., vol.13, No. 1, p. 210 (1991).

Smith, K.R., et al., *Computer Methods for Improved Diagnostic Image Display Applied to Stereotactic Neurosurgery*, Automedical, vol. 14, pp. 371–386 (1991).

Smith, K.R., et al., *The Neurostation™—a highly, accurate, minimally invasive solution to frameless stereotatic neurosurgery*, Comput. Med. Imag. and Graph., vol. 18, No. 4, pp. 247–256 (1994).

\* cited by examiner

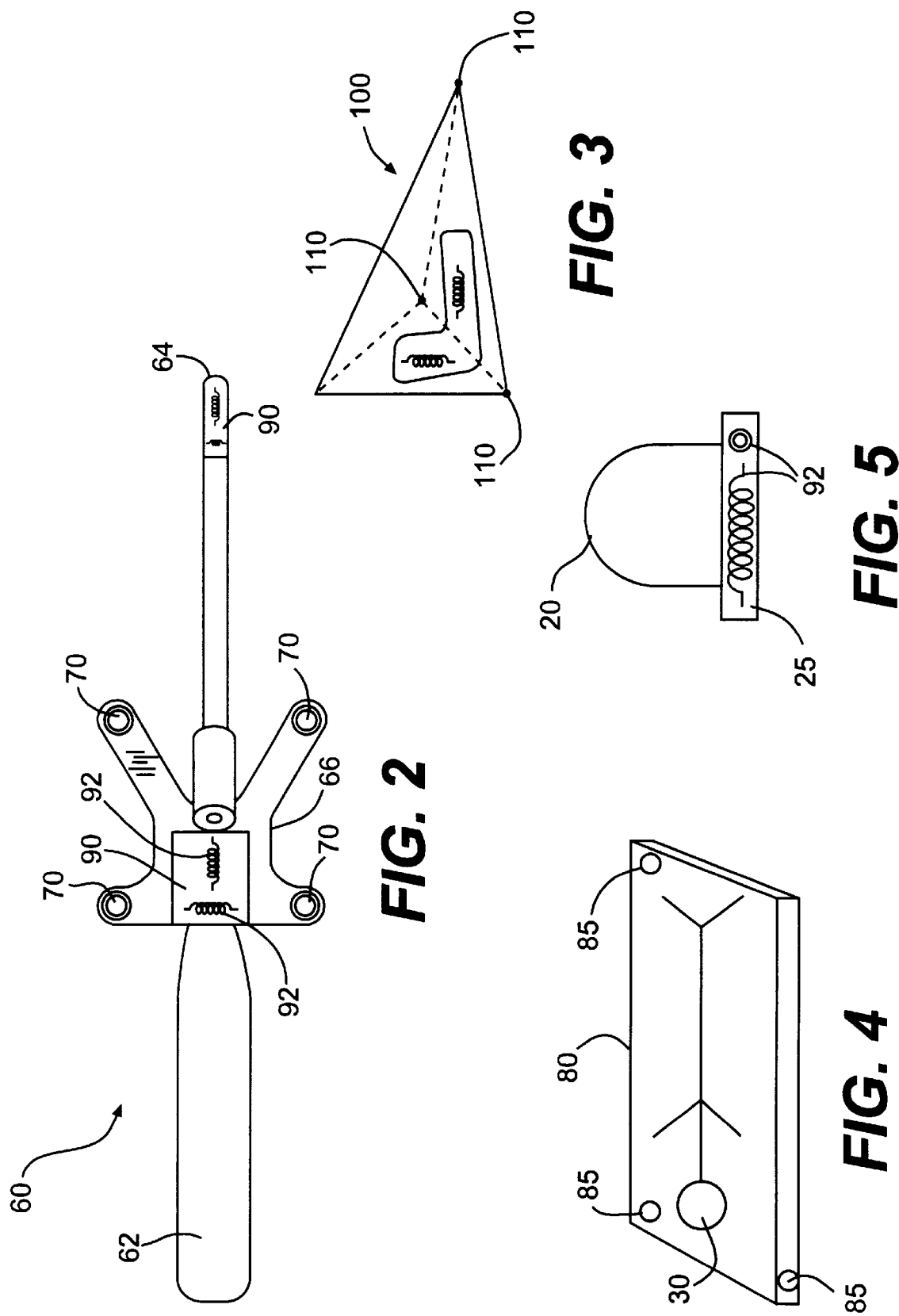

SYSTEM FOR TRANSLATION OF ELECTROMAGNETIC AND OPTICAL LOCALIZATION SYSTEMS

CONCURRENTLY FILED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; Surgical Communication and Power System, by Mark W. Hunter, Paul Kessman and Brad Jascob; and Surgical Sensor, by Mark W. Hunter, Sheri McCoid and Paul Kessman.

BACKGROUND OF THE INVENTION

1. Field of the Invention

The present invention relates to localization of a position during surgery. The present invention relates more specifically to a system that facilitates combined electromagnetic and optical localization of a position during stereotactic surgery, such as brain surgery and spinal surgery.

2. Description of Related Art

Precise localization of a position has always been important to stereotactic surgery. In addition, minimizing invasiveness of surgery is important to reduce health risks for a patient. Stereotactic surgery minimizes invasiveness of surgical procedures by allowing a device to be guided through tissue that has been localized by preoperative scanning techniques, such as for example, MR, CT, ultrasound, fluoro and PET. Recent developments in stereotactic surgery have increased localization precision and helped minimize invasiveness of surgery.

Stereotactic surgery is now commonly used in surgery of the brain. Such methods typically involve acquiring image data by placing fiducial markers on the patient's head, scanning the patient's head, attaching a headring to the patient's head, and determining the spatial relation of the image data to the headring by, for example, registration of the fiducial markers. Registration of the fiducial markers relates the information in the scanned image data for the patient's brain to the brain itself, and utilizes one-to-one mapping between the fiducial markers as identified in the image data and the fiducial markers that remain on the patient's head after scanning and throughout surgery. This is referred to as registering image space to patient space. Often, the image space must also be registered to another image space. Registration is accomplished through knowledge of the coordinate vectors of at least three non-collinear points in the image space and the patient space.

Currently, registration for image guided surgery is completed by a few different methods. First, point-to-point registration is accomplished by the user to identify points in image space and then touch the same points in patient space. Second, surface registration involves the user's generation of a surface (e.g., the patient's forehead) in patient space by either selecting multiple points or scanning, and then accepting or rejecting the best fit to that surface in image space, as chosen by the processor. Third, repeat fixation devices entail the user repeatedly removing and replacing a device in known relation to the fiducial markers. Such registration methods have additional steps during the procedure, and therefore increase the complexity of the system and increase opportunities for introduction of human error.

Through the image data, quantitative coordinates of targets within the patient's body can be specified relative to the fiducial markers. Once a guide probe or other instrument has been registered to the fiducial markers on the patient's body, the instrument can be navigated through the patient's body using image data.

It is also known to display large, three-dimensional data sets of image data in an operating room or in the direct field of view of a surgical microscope. Accordingly, a graphical representation of instrument navigation through the patient's body is displayed on a computer screen based on reconstructed images of scanned image data.

Although scanners provide valuable information for stereotactic surgery, improved accuracy in defining the position of the target with respect to an accessible reference location can be desirable. Inaccuracies in defining the target position create inaccuracies in placing a therapeutic probe. One method for attempting to limit inaccuracies in defining the target position involves fixing the patient's head to the scanner to preserve the reference. Such fixation may be uncomfortable for the patient and creates other inconveniences, particularly if surgical procedures are involved. Consequently, a need exists for a system utilizing a scanner to accurately locate positions of targets, which allows the patient to be removed from the scanner.

Stereotactic surgery utilizing a three-dimensional digitizer allows a patient to be removed from the scanner while still maintaining a high degree of accuracy for locating the position of targets. The three-dimensional digitizer is used as a localizer to determine the intra-procedural relative positions of the target. Three-dimensional digitizers may employ optical, acoustic, electromagnetic or other three-dimensional navigation technology for navigation through the patient space.

Different navigational systems have different advantages and disadvantages. For example, electromagnetic navigation systems do not require line-of-sight between the tracking system components. Thus, electromagnetic navigation is beneficial for laproscopic and percutaneous procedures where the part of the instrument tracked cannot be kept in the line-of sight of the other navigation system components. Since electromagnetic navigation allows a tracking element to be placed at the tip of an instrument, electromagnetic navigation allows the use of non-rigid instruments such as flexible endoscopes. However, use of certain materials in procedures employing electromagnetic tracking is disadvantageous since certain materials could affect the electromagnetic fields used for navigation and therefore affect system accuracy.

Comparatively, optical navigation systems have a larger working volume than electromagnetic navigation systems, and can be used with instruments having any material composition. However, the nature of optical navigation systems does not accommodate tracking system components on any portion of an instrument to be inserted into the patient's body. For percutaneous and laproscopic procedures, optical navigation systems typically track portions of the system components that are in the system's line of sight, and then determine the position of any non-visible portions of those components based on system parameters. For example, an optical navigation system can track the handle of a surgical instrument but not the inserted tip of the surgical instrument, thus the navigation system must track the instrument handle and use predetermined measurements of the device to determine where the tip of the instrument is relative to the handle. This technique cannot be used for flexible instruments since the relation between the handle and the tip varies.

Stereotactic surgery techniques are also utilized for spinal surgery, in order to increase accuracy of the surgery and minimize invasiveness. Accuracy is particularly difficult in spinal surgery and must be accommodated in registration and localization techniques utilized in the surgery. Prior to spinal surgery, the vertebra are scanned to determine their alignment and positioning. During imaging, scans are taken at intervals through the vertebra to create a three-dimensional pre-procedural data set for the vertebra. However, after scanning the patient must be moved to the operating table, causing repositioning of the vertebra. In addition, the respective positions of the vertebra may shift once the patient has been immobilized on the operating table because, unlike the brain, the spine is not held relatively still by a skull-like enveloping structure. Even normal patient respiration may cause relative movement of the vertebra.

Computer processes discriminate the image data retrieved by scanning the spine so that the body vertebra remain in memory. Once the vertebra are each defined as a single rigid body, the vertebra can be repositioned with software algorithms that define a displaced image data set. Each rigid body element has at least three fiducial markers that are visible on the pre-procedural images and accurately detectable during the procedure. It is preferable to select reference points on the spinous process that are routinely exposed during such surgery.

See also, for example, U.S. Pat. No. 5,871,445, WO 96/11624, U.S. Pat. No. 5,592,939 and U.S. Pat. No. 5,697,377, the disclosures of which are incorporated herein by reference.

SUMMARY OF THE INVENTION

To enhance the prior art, and in accordance with the purposes of the invention, as embodied and broadly described herein, there is provided a system for utilizing and registering at least two surgical navigation systems during stereotactic surgery. The system comprises a first surgical navigation system defining a first patient space, a second surgical navigation system defining a second patient space, and a translation device to register the coordinates of the first patient space to the coordinates of the second patient space. The translation device comprises a rigid body, at least one component for a first navigation system placed in or on the rigid body, and at least one component for a second navigation system placed in or on the rigid body, in known relation to the at least one component for the first navigation system. The translation device is positioned in a working volume of each of the at least two navigation systems Additional features and advantages of the invention will be set forth in the description which follows, and in part will be apparent from the description, or may be learned from practice of the invention. The objectives and other advantages of the invention will be realized and attained by the apparatus particularly pointed out in the written description and claims herein as well as the appended drawings.

BRIEF DESCRIPTION OF THE DRAWINGS

The accompanying drawings, which are incorporated in and constitute part of the specification, illustrate a presently preferred embodiment of the invention and together with the general description given above and detailed description of the preferred embodiment given below, serve to explain the principles of the invention.

FIG. 2 illustrates a top view of a first embodiment of an optical-to-electromagnetic translation device;

FIG. 3 illustrates a schematic perspective view of a second embodiment of an optical-to-electromagnetic translation device;

FIG. 4 illustrates a schematic perspective view of a third embodiment of an optical-to-electromagnetic translation device; and FIG. 5 illustrates a schematic perspective view of a fourth embodiment of an optical-to-electromagnetic translation device.

DESCRIPTION OF THE PREFERRED EMBODIMENTS

Figure 1:
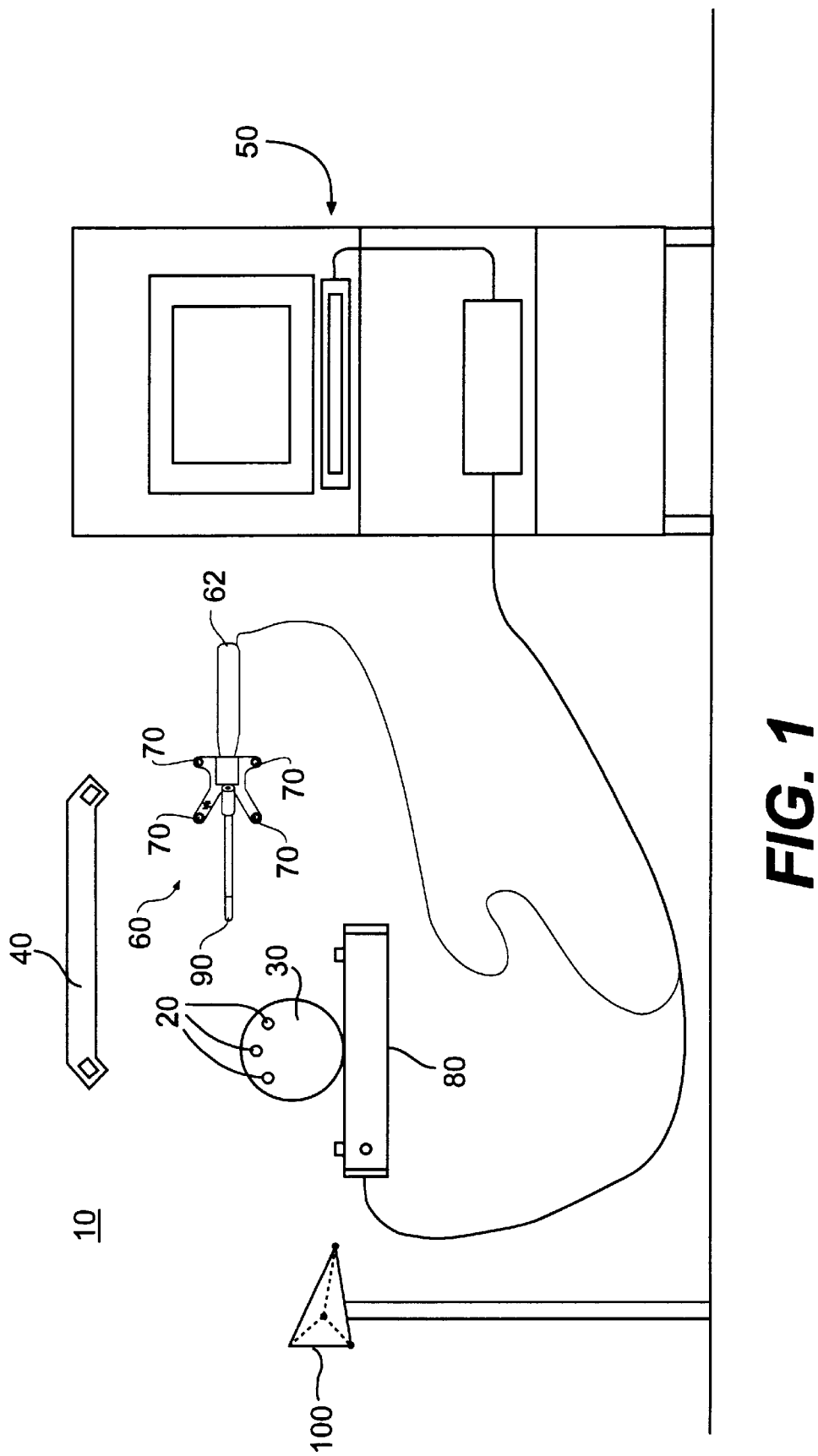
FIG. 1 is a schematic diagram illustrating an embodiment of the system that facilitates combined electromagnetic and optical localization of a position during stereotactic surgery according to the present invention.

Reference will now be made in detail to the present preferred exemplary embodiments of the invention, examples of which are illustrated in the accompanying drawings. Wherever possible, the same reference numbers will be used throughout the drawings to refer to the same or like parts.

The present invention contemplates a system for stereotactic surgery comprising a first surgical navigation system defining a first patient space, a second surgical navigation system defining a second patient space, a translation device to register (correlate the coordinates of) the first patient space to the second patient space, and an image data set generated from a scanning device that defines an image space. The image space is registered to at least one of the first and second patient spaces.

An exemplary embodiment of the system 10 of the present invention is illustrated in FIG. 1. The system of the present invention will be discussed hereinafter with respect to a an optical navigation system in combination with an electromagnetic navigation system. However, the present invention similarly contemplates combining any two navigation systems including optical, acoustic, electromagnetic, or conductive.

The system illustrated in FIG. 1 includes a first navigation system that is optical. Elements of the optical navigation system include at least one optical element, and an optical receiving array 40 in line-of-sight communication with the optical element and in communication with a computer system 50. The optical element can either generate an optical signal independently or alternatively generate an optical signal by reflecting a signal received from an optical signal source. The line-of-sight of the optical receiving array defines a "working volume" of the optical system, which is the space in which the optical system can effectively navigate.

At least one optical element is placed on a translation device. According to the illustrated embodiment of the present invention, preferably at least three non-collinear optical elements are utilized by the system in order to obtain six degrees of freedom location and orientation information from the optical elements.

In the exemplary embodiment of the invention illustrated in FIG. 1, four embodiments of the translation device 20, 60, 80, 100 are shown in the working volume of the optical system. While only one translation device is needed for proper operation of the translation system of the present invention, the present invention also contemplates the use of more than one translation device for registration of different navigation systems. For example, more than one translation device could be used for redundant registration of two navigation systems in order to obtain increased accuracy of registration. In addition, if three different navigation systems were utilized in a single surgical procedure, one translation device could be used to register (i.e., correlate the coordinates of) all three navigation systems, or one translation device could be used to register the first and second navigation systems while another translation device registered the second and third navigation systems.

As illustrated in FIGS. 1 and 2, a dynamic translation device can be incorporated into a medical instrument 60 for use in the surgical procedure being navigated. The medical instrument 60 includes a handle 62, a tip portion 64 and a localization frame 66. At least three collinear optical elements 70 (capable of defining six degrees of freedom in the optical system) are placed on the localization frame for communication with the optical receiving array 40. As the medical instrument moves in the working volume of the optical system, the optical receiving array 40 sends a signal to the computer system 50 indicating the current position of the medical instrument 60.

As illustrated in FIGS. 1 and 3, a translation device can also be incorporated into a rigid static translation device 100 that is added to the optical and electromagnetic navigation system working spaces specifically to register (i.e., correlate the coordinates of) the optical navigation system to the electromagnetic navigation system. The static translation device may have any configuration allowing optical elements 110 to be placed in such a manner to define six degrees of freedom in the optical system (e.g., three non-collinear optical elements). Although this embodiment provides a suitable translation device, it also adds undesirable complexity to the navigation systems by requiring the navigation systems to receive input from and identify an additional structure in their working volume.

As illustrated in FIGS. 1 and 4, a translation device can also be incorporated into the operating table. Optical elements 85 defining six degrees of freedom in the optical system are placed on the operating table in such a manner that they will remain in the line-of-sight of the optical receiving array 40 during the procedure.

As illustrated in FIGS. 1 and 5, a dynamic translation device can further be incorporated into one or more of the optical elements 20 placed on the patient 30 (or mounted to the patient via a frame).

It is to be understood that optical elements 20, 70 may be placed on the patient 30 or on the medical instrument 60 for tracking movement of the patient 30 and/or the medical instrument 60 during the procedure, even if the optical elements 20, 70 on the patient 30 and the medical instrument 60 are not used as translation devices.

As illustrated in FIG. 1, the system of the present invention also includes a second navigation system. In the embodiment illustrated in FIG. 1, the second navigation system is electromagnetic. Thus, any translation device also has at least one component for the electromagnetic navigation system that is in known relationship to the optical elements placed on the device. The known relation of the optical and electromagnetic elements is received by the computer system 50 so that the computer system can generate a translation matrix for registration (i.e., correlation of the coordinates) of the optical and electromagnetic navigation systems. Elements of the illustrated electromagnetic navigation system include an electromagnetic element 90 (e.g., a sensor having at least one coil 92), and a magnetic field generator. In the embodiment shown in FIG. 1, the magnetic field generator is provided in the operating table 80. Therefore, in the embodiment of the translation device shown in FIG. 4, as described above, the magnetic field generator in the operating table 80 serves as the electromagnetic element on the translation device when placed in known relation to the optical elements 85 placed on the table 80. The known relation of the optical and electromagnetic elements is received by the computer system 50 so that the computer system can generate a translation matrix for correlation of the optical and electromagnetic navigation system coordinates.

In the medical instrument 60 embodiment of the translation device illustrated in FIG. 2, the electromagnetic element 90 is preferably a sensor having at least one coil 92. The sensor includes two coils 92 that are placed perpendicular to each other to create a sensor having six degrees of freedom. The sensor is placed in or on the localization frame 66 in known relation to the optical elements 70. The known relation of the optical and electromagnetic elements is received by the computer system 50 so that the computer system can generate a translation matrix for correlation of the optical and electromagnetic navigation system coordinates.

In the rigid static embodiment 100 of the translation device illustrated in FIG. 3, the electromagnetic element 90 is preferably a sensor as described above with respect to FIG. 2, placed in or on the rigid static device 100 in known relation to the optical elements 110. The known relation of the optical and electromagnetic elements is received by the computer system 50 so that the computer system can generate a translation matrix for correlation of the optical and electromagnetic navigation system coordinates.

As illustrated in FIG. 5, showing a schematic version of a dynamic translation device to be integrated one or more of the optical elements 20 placed on the patient 30 (or mounted to the patient via a frame), the electromagnetic element 90 is preferably a sensor as described above with respect to FIG. 2. The sensor is preferably placed in or on the base 25 in known relation to the optical element 20. The known relation of the optical and electromagnetic elements is received by the computer system 50 so that the computer system can generate a translation matrix for correlation of the optical and electromagnetic navigation system coordinates. Although the embodiment of FIG. 5 shows the electromagnetic element being integrated with the optical element, the electromagnetic element may alternatively be attached to or interchanged with the optical element 20 placed on the patient 30 (or mounted to the patient via a frame).

It is to be understood that an electromagnetic element 90 may be placed on the patient 30 or on the medical instrument 60 for tracking movement of the patient 30 and or the medical instrument 60 during the procedure, even if the electromagnetic element 90 on the patient 30 and the medical instrument 60 is not used as translation devices.

An exemplary operation of the system of the present invention will now be described. For the purposes of the example, the procedure is brain surgery and the translation device is only included in the medical instrument 60, as illustrated in FIG. 2. An optical navigation system and an electromagnetic navigation system are used.

Prior to the surgical procedure, fiducial markers are placed on the patient's head and the patient's head is scanned using, for example, a MR, CT, ultrasound, fluoro or PET scanner. The scanner generates an image data set including data points corresponding to the fiducial markers. The image data set is received and stored by the computer system.

After the patient's head has been scanned, the patient is placed on the operating table and the navigation systems are turned on. In brain surgery, the navigation systems track movement of the patients head and movement of the medical instrument. Since the medical instrument is used as the translation device, both optical and electromagnetic navigation system elements are placed on the medical instrument and both the optical and electromagnetic systems track movement of the medical instrument.

Since the patient's head must also be tracked, either optical or electromagnetic navigation system elements must be placed on the patient's head. For the purposes of the present illustration, optical elements are placed on the patient's head. Since the optical navigation system is tracking movement of the patient's head, the optical navigation system's patient space must be registered to the image space defined by the pre-operative scan.

After the optical navigation system patient space has been registered to the image space, the electromagnetic navigation system patient space must be registered to the optical navigation system patient space. Having a known relation between the electromagnetic and optical elements in the medical instrument allows the computer to use a translation matrix to register the optical navigation system patient space to the electromagnetic navigation system patient space. Thus, the electromagnetic navigation patient space is registered to the image space.

If the medical instrument has a rigid design, knowing the dimensions of the medical instrument and the orientation and location of the localization frame 66 allows the computer system to determine the position of the tip of the medical instrument. However, in the case where the medical instrument 60 has a non-rigid design, merely knowing the location and orientation of the localization frame 66 by tracking the position of the optical and electromagnetic elements cannot allow the computer to determine the position of the tip 64 of the instrument. Additionally, optical navigation systems are line-of-sight navigation systems and therefore do not allow direct tracking of the tip of a probe once it has been inserted into the patient (because the tip is out of the line-of sight of the optical receiving array).

However, electromagnetic navigation systems do not require line-of-sight and therefore can track the location and orientation of the inserted tip of even a non-rigid medical instrument. To do so, an electromagnetic element 90 is placed in the tip portion 64 of the medical instrument and is tracked by the electromagnetic navigation system. Since the electromagnetic navigation system patient space has been registered to the image space, movement of the tip of the medical instrument within the patient's brain (within the image space) can be tracked.

Thus, the present invention allows increased accuracy and flexibility for users by utilizing the features of multiple navigation system to their respective advantages. In addition, utilizing multiple navigation systems often increases the overall working volume during the procedure.

It will be apparent to those skilled in the art that various modifications and variations can be made to the system of the present invention without departing from the scope or spirit of the invention. Thus, it is intended that the present invention cover the modifications and variations of this invention provided they come within the scope of the appended claims and their equivalents.

What is claimed is:

1. A system for utilizing and registering at least two surgical navigation systems during stereotactic surgery, the system comprising:
    a first surgical navigation system defining a first patient space;
    a second surgical navigation system defining a second patient space; and
    a translation device to register the coordinates of the first patient space to the coordinates of the second patient space.

2. The system of claim 1, wherein the first navigation system is a line-of-sight navigation system.

3. The system of claim 2, wherein the line-of-sight navigation system is an optical navigation system.

4. The system of claim 2, wherein the second navigation system is a non-line-of-sight navigation system.

5. The system of claim 4, wherein the non-line-of sight system is an electromagnetic navigation system.

6. The system of claim 1, wherein the translation device includes at least one component for the first navigation system and at least one component for the second navigation system.

7. The system of claim 6, wherein a translation matrix between the at least one component for the first navigation system and the at least one component of the second navigation system is predetermined.

8. The system of claim 7, wherein the first navigation system is an optical navigation system and the at least one components for the first navigation system is an optical element.

9. The system of claim 8, wherein the second navigation system is an electromagnetic navigation system and the at least one component for the second navigation system is an electromagnetic element.

10. The system of claim 8, wherein the second navigation system is an electromagnetic navigation system, and wherein the at least one component for the second navigation system includes at least one sensor.

11. A device for registering coordinates of at least two navigation systems, the device comprising:
    at least one component for a first navigation system placed in or on the rigid body; and
    at least one component for a second navigation system placed in or on the rigid body, in known relation to the at least one component for the first navigation system,
    wherein the device is positioned in a working volume of each of the at least two navigation systems.

12. The device of claim 11, wherein the first navigation system is a line-of line-of-sight navigation system.

13. The system of claim 12, wherein the line-of-sight navigation system is an optical navigation system.

14. The system of claim 12, wherein the second navigation system is a non-line-of-sight navigation system.

15. The system of claim 14, wherein the non-line-of sight system is an electromagnetic navigation system.

16. The system of claim 11, wherein the first navigation system is an optical navigation system and the at least one component for the first navigation system is an optical element.

17. The system of claim 16, wherein the second navigation system is an electromagnetic navigation system and the at least one component for the second navigation system is an electromagnetic element.

18. The system of claim 9, wherein the electromagnetic element is a sensor.

19. The system of claim 9, wherein the electromagnetic element generates an electromagnetic field.

* * * * *

UNITED STATES PATENT AND TRADEMARK OFFICE
CERTIFICATE OF CORRECTION

| | |
|---|---|
| PATENT NO. : 6,235,038 B1 | Page 1 of 1 |
| DATED : May 22, 2001 | |
| INVENTOR(S) : Mark W. Hunter et al. | |

It is certified that error appears in the above-identified patent and that said Letters Patent is hereby corrected as shown below:

Column 8, claim 11,
Between lines 45 and 46, after "comprising:" and before "at least one component for a first navigation system", insert -- a rigid body; --.

Column 8, claim 12,
Line 55, "line-of line-of-sight" should read -- line-of-sight --.

Signed and Sealed this

Nineteenth Day of March, 2002

Attest:

Attesting Officer

JAMES E. ROGAN
Director of the United States Patent and Trademark Office